US010893866B2

(12) United States Patent
Xu et al.

(10) Patent No.: US 10,893,866 B2
(45) Date of Patent: Jan. 19, 2021

(54) REVERSIBLE, NON-INVASIVE, WOUND CLOSURE SYSTEM AND METHOD

(71) Applicants: Shidong Xu, Boston, MA (US); Shizhong Xu, Boston, MA (US)

(72) Inventors: Shidong Xu, Boston, MA (US); Shizhong Xu, Boston, MA (US)

( * ) Notice: Subject to any disclaimer, the term of this patent is extended or adjusted under 35 U.S.C. 154(b) by 167 days.

(21) Appl. No.: 15/936,413

(22) Filed: Mar. 26, 2018

(65) Prior Publication Data

US 2019/0290278 A1  Sep. 26, 2019

(51) Int. Cl.
*A61B 17/08* (2006.01)
*A61B 17/00* (2006.01)

(52) U.S. Cl.
CPC .. *A61B 17/085* (2013.01); *A61B 2017/00889* (2013.01); *A61B 2017/081* (2013.01); *A61B 2017/086* (2013.01)

(58) Field of Classification Search
CPC . A61B 17/08; A61B 17/085; A61B 17/00491; A61B 2017/00889; A61B 2017/081
See application file for complete search history.

(56) References Cited

U.S. PATENT DOCUMENTS

| 6,329,564 | B1 * | 12/2001 | Lebner | A61B 17/085 602/41 |
| 7,838,718 | B2 * | 11/2010 | Lebner | A61B 17/085 602/41 |
| 8,636,763 | B2 * | 1/2014 | Lebner | A61B 17/085 602/41 |
| 8,764,792 | B2 * | 7/2014 | Weiser | A61B 17/085 602/42 |
| 2002/0099315 | A1 * | 7/2002 | Lebner | A61B 17/085 602/54 |
| 2004/0204740 | A1 * | 10/2004 | Weiser | A61B 17/085 606/213 |
| 2008/0228219 | A1 * | 9/2008 | Weiser | A61B 17/085 606/215 |
| 2010/0228287 | A1 * | 9/2010 | Jeekel | A61B 17/085 606/215 |
| 2019/0343524 | A1 * | 11/2019 | Weiser | A61L 24/043 |

* cited by examiner

*Primary Examiner* — George J Ulsh
(74) *Attorney, Agent, or Firm* — Ariel S. Bentolila; Bay Area IP Group, LLC

(57) ABSTRACT

A system including a first base sheet, a second base sheet, a first plurality of individual strip sections extending out of said first base sheet, a second plurality of individual strip sections extending out of the second base sheet, wherein said first plurality of individual strip sections are operable for engagement and disengagement with said second base sheet and wherein said second plurality of individual strip sections are operable for engagement and disengagement with said first base sheet to enable and maintain wound closure and allow application of antibiotics to prevent and/or treat wound infection or application of other topical agents without removing and replacing the system.

1 Claim, 8 Drawing Sheets

REVERSIBLE, NON-INVASIVE, WOUND CLOSURE SYSTEM AND METHOD

CROSS-REFERENCE TO RELATED APPLICATIONS

Not applicable

RELATED CO-PENDING U.S. PATENT APPLICATIONS

Not applicable

INCORPORATION BY REFERENCE OF SEQUENCE LISTING PROVIDED AS A TEXT FILE

Not applicable

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to wound closure systems for various wound types. More particularly, certain embodiments of the invention relate to a system and method for wound closure and wound care.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Closure of tissue openings including surgical incisions and accidental lacerations or wounds, may be critical to minimize the risk of infection and promote optimal healing of the wound or incision. Closing a tissue opening or wound requires a related mechanism for drawing both sides of a tissue opening together to promote healing and to reduce the formation of scar tissue.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that a number of bandage type devices exist for sutureless closing of wounds. The object of these devices is to close and secure a wound without the use of sutures requiring needle punctures in the vicinity of the wound and the possibility of secondary infections, and additional discomfort to the patient. Strips and glues may cover skin edges and hold them adjacent. Surgical glue is also used. Such an approach has only been proven adequate for small wounds where skin edges are not widely separated or under tension during closure.

Typical wound closure mechanisms include passing various categories of materials through the skin, such as staples and sutures. Common methods for closing tissue openings caused by lacerations or surgical incisions are suturing and stapling. Both of these procedures are invasive, which can traumatize and compromise the integrity of the tissue opening and the nutrient blood supply to the healing tissue edges. Suturing or stapling cause pain, increase the possibility of infection, expose the surgeon, as well as the patient, to blood-borne disease, leave behind scars, and require a follow-up visit for suture or staple removal.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
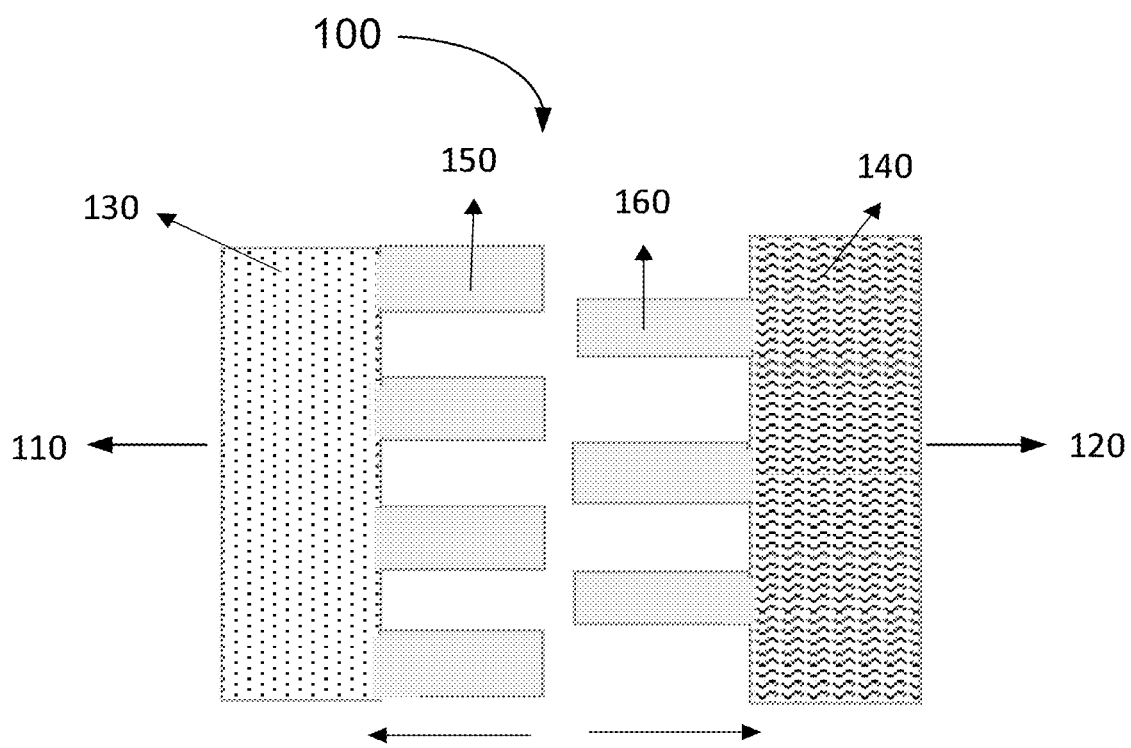
FIG. 1 is a perspective view of a Reversible Wound Closure System, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is a well settled law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of Claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" include the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like.

It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising" And "contain" and variations of them— Such terms are open-ended and mean "including but not limited to". When employed in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

All terms of exemplary language (e.g., including, without limitation, "such as", "like", "for example", "for instance", "similar to", etc.) are not exclusive of any other, potentially, unrelated, types of examples; thus, implicitly mean "by way of example, and not limitation . . . ", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the disclosed and claimed subject matter may include the use of either of the other two terms.

Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Some embodiments of the present invention and variations thereof, relate to wound closure systems and methods. In one embodiment of the present invention, the wound closure system and method includes a reversible, non-invasive, closing device for various types of surgical incisions, non-surgical incisions, traumatic lacerations, and various types and shapes of wounds that may require closure of the wound and stop a spread of infection. The reversible, non-invasive, interlacing wound closure system may be used for wound approximation, wound closure, and wound care by allowing the application of topical wound care products such as antibiotics, and healing-promoting agents. The system may be used in all types of wounds. The system may be used for clean surgical incisions and lacerations which require precise approximation and or preventative topical antibiotic treatment. The system may be used for wounds with wide open edges and infection and require frequent topical wound care treatments. The system may be used for Primary Closure, Secondary closure, and Tertiary (delayed) closure.

Problems associated with invasive wound closure devices such as conventional sutures and/or staples may include secondary infection, tissue reaction, discomfort, cost, anesthesia, and unsightly scars resulting from needle punctures of conventional suturing, needle puncture marks, suture scarring, track marks, and crosshatch marks. Less precise wound approximation may occur for staples. In some embodiments, the reversible, atraumatic, and non-invasive closing device for wound closure and wound care is a needleless suturing device which allows both the approximation of wound edges and with reversible wound closure, and application/renewal of topical wound care products to treat/prevent wound infection and promote wound healing.

Surgical incision site infections may account for up to 20 percent of all of healthcare-associated infections. At least five percent of patients who have a surgical procedure may go on to develop a surgical incision site infection, highlighting the importance of good prevention, detection and management. Superficial surgical site infections may delay healing, impair cosmetic outcome and potentially cause other morbidity, such as deeper infections, as well as potentially increasing costs, and the consumption of healthcare resources. In some embodiments, topical agents may be applied during wound healing. Topical agents may include wound healing promoting agents but not limited to, adhesives such as bio-adhesives (e.g. fibrin and other tissue sealants) and super glues (e.g. cyanoacrylates), to come directly into contact with the surface near the wound's edges.

In other embodiments, the reversible, non-invasive, wound closure system may provide reinforcement to increase the tensile strength and decrease the risks of dehiscence associated with skin adhesives (e.g. glue) by holding wound or incision edges together with interlacing or interweaving strips. The wound closure system may be used in all types of wounds such as clean or contaminated, surgical and non-surgical, traumatic lacerations, and/or chronic wounds that may require frequent wound care. The wound closure system may be used in settings ranging from the operating or emergency room to out in the field. The wound closure system may be used for Primary Closure, Secondary closure, and Tertiary (delayed) closure. The wound closure system may be used for skin closure of all types of clean or contaminated surgical incisions (Class I-IV) that require topical antiseptics (propylactic or therapeutic), pain control, and wound healing promoting agents. It may also be applied to non-surgical, chronic, wounds or traumatic lacerations that need strong holding support and application of topical wound care products.

In some embodiments, the reversible, non-invasive, wound closure system may enable a fast closing of a wound, may leave no unsightly scars resulting from needle or staple punctures, may not need anesthetizing a patient or numbing of injured area to close the wound, such as is necessary in most cases where suturing is done by a needle and thread, and there being no further injury to the skin around a wound, as is sometimes the case when suturing with a needle or staple, and in attempt to close a wound tightly, the needle and thread sutures are placed as close as possible to the edge of the wound so that sometimes the needle tears the skin from the penetration point out to the edge of the wound.

In other embodiments, the reversible, non-invasive, wound closure system may allow application and renewal of topical wound care agents (antibiotics, pain control, healing promoting agents) without peeling off the entire closure device from the skin. In use, for surgical incision or laceration wounds, apply one base sheet along an edge of the wound with adhesive side face down, approximately 1 mm-2 mm back from skin edge. Apply force to adhere the base sheet to the skin. Apply a 2nd base sheet (mate) to the edge of the opposite side of the wound. Grab pulling ends of strips/fingers on both sides and pull in opposing directions so the strips/fingers are interlaced/interweaved and the wound edges are drawn together.

In additional embodiments, the reversible, non-invasive, wound closure system may allow application/renewal of topical antibiotics to prevent and or treat wound infection while maintaining wound closure and without removing and replacing the closure device. The system may allow application/renewal of wound care products to promote healing while maintaining wound closure and without removing/replacing the closure device. Topical agents or wound care products, such as skin adhesives may be applied stepwise as strips are opened and closed consecutively during wound healing process. The system may allow wound approximation with even closing pressure from both sides of the wound. The system may be used for various types of wounds for primary, secondary, and tertiary closures, and may be used in a variety of settings, including but not limited to the operating room, emergency room, wound care center, trauma center, battle fields, or as part of the first aid kits.

FIG. 1 is a perspective view of a Reversible Wound Closure System 100, in accordance with an embodiment of the present invention. The present embodiment shows a first base sheet 110 having an upper surface and under surface portions, an array of hook materials 130 disposed on the upper surface portion of the first base sheet 110, a second base sheet 120 having an upper surface and under surface portions, an array of loop materials 140 is disposed on the upper surface portion of the second base sheet 120. A first plurality of fingers or strip sections 150 extending out of the first base sheet 110 includes an array of mating hook materials 210 (FIG. 2) disposed on an under surface portion of the first plurality of strip sections 150. The array of mating hook materials 210 of the first plurality of strip sections 150 are operable for engagement with the array of loop materials 140 disposed on the upper surface portion of the second base sheet 120. A second plurality of fingers or strip sections 160 extending out of the second base sheet 120 includes an array of mating loop materials 220 (FIG. 2) disposed on an under surface portion of the second plurality of strip sections 160. The array of mating loop materials 220 of the second plurality of strip sections 160 are operable for engagement with the array of hook materials 130 disposed on the upper surface portion of the first base sheet 110. A skin compatible self-adhesive material is disposed on the under surface portions of the first and second base sheet 110 120 where the under surface portions of the first and second base sheets 110 120 facing the skin may be coated with medical grade, hypoallergenic, and/or non-latex adhesives which may affix the base sheets securely to the skin adjacent the wound and lock the device in its closed position.

In some embodiments, the first plurality of strip sections 150 include at least four (4) fingers or strip sections 150 and the second plurality of strip sections 160 include at least three (3) fingers or strip sections 160. In an alternative embodiment, the first plurality of strip sections 150 may include less than or more than four (4) fingers or strip sections 150 and the second plurality of strip sections 160 may include less than or more than three (3) fingers or strip sections 160 depending on length or size of, but not limited to, a wound, surgical incision, non-surgical incision, or laceration.

Figure 2:
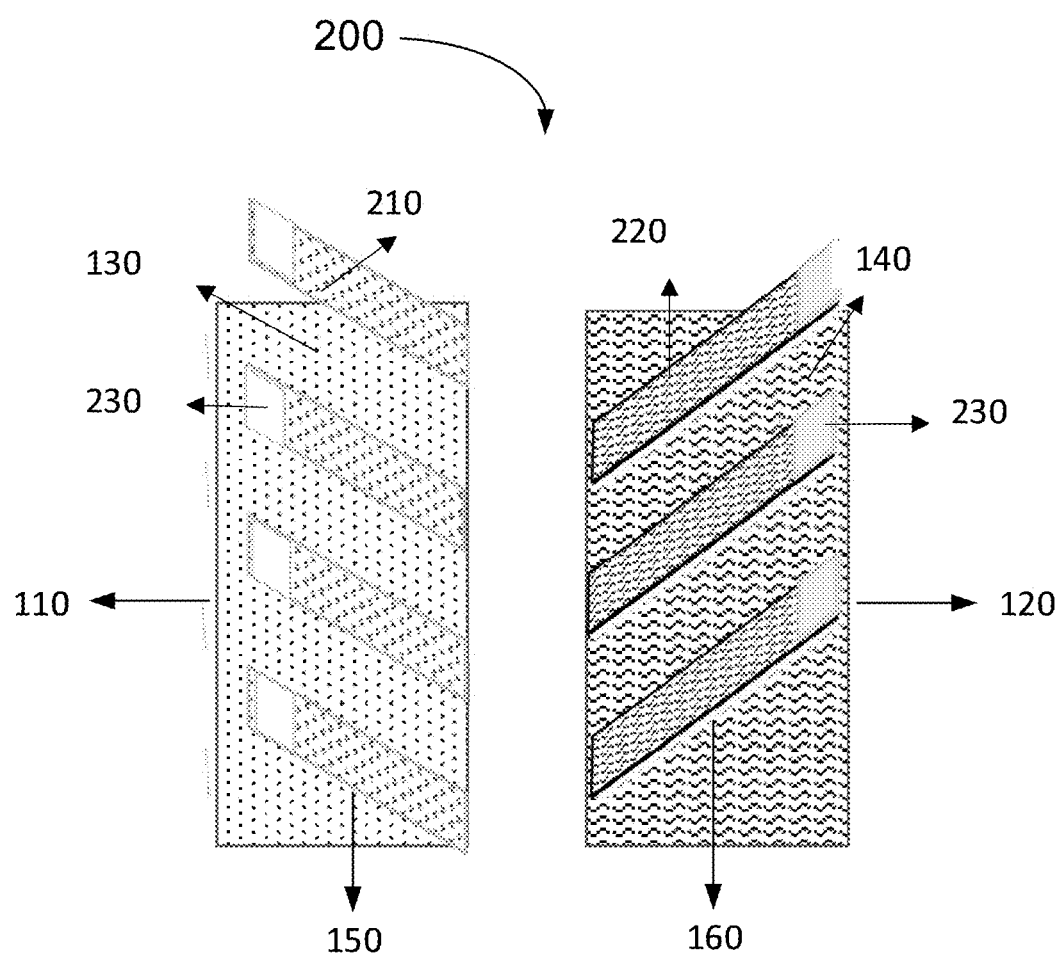
FIG. 2 is a 3-D view of the Reversible Wound Closure System, in accordance with an embodiment of the present invention.

FIG. 2 is a 3-D view 200 of the Reversible Wound Closure System 100, in accordance with an embodiment of the present invention. In the present embodiment shown, the first plurality of strip sections 150 are folded laterally showing the under surface/underside portion of the strip sections 150 and the second plurality of strip sections 160 are folded laterally showing the under surface portion of the strip sections 160. The underside portion of each of the first plurality of strip sections 150 includes an array of mating hook materials 210 and the underside portion of each of the second plurality of strip sections 160 includes an array of mating loop materials 220. An end portion of each strip section includes a tab implement 230 without a patch of hook or loop material which may aid in closing or opening of the strip sections from an engagement with the base sheet.

In some embodiments, the array of hook materials 130 disposed on an upper surface portion of the first base sheet 110 may be complementary and may engage with the array of loop materials 140 disposed on the upper surface portion of a second base sheet 120, which may affect a joining of the first and second base sheet. The array of hook materials 210 of the first plurality of strip sections 150 may be complementary and may engage with the array of mating loop materials 140 disposed on the upper surface portion of the second base sheet 120, which may affect a joining of the first plurality of strip sections 150 and second base sheet 120. The array of loop materials 220 of the second plurality of strip sections 160 may be complementary and may engage with the array of hook materials 130 disposed on the upper surface portion of the first base sheet 110, which may affect a joining of the second plurality of strip sections 160 and the first base sheet 110.

Figure 3:
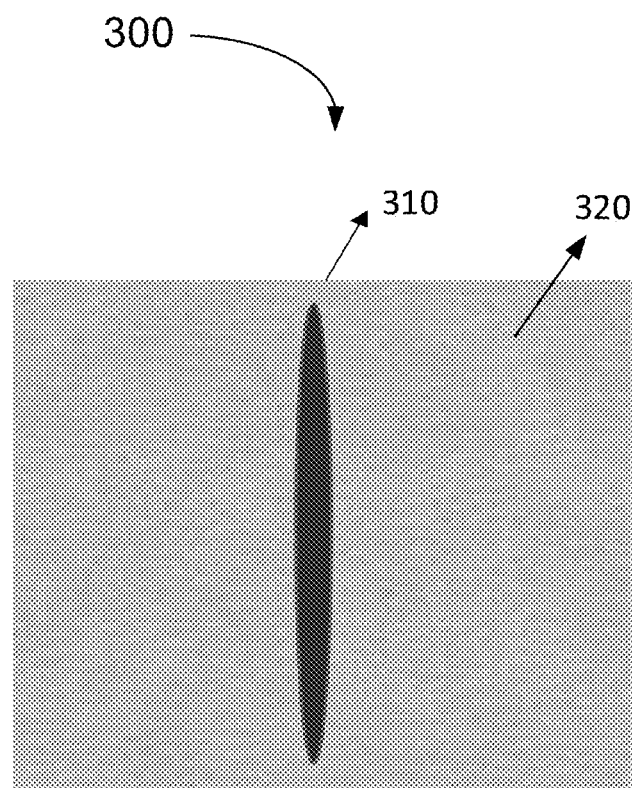
FIG. 3 is an illustration of a surgical incision, in accordance with an embodiment of the present invention.

FIG. 3 is an illustration of a surgical incision 300, in accordance with an embodiment of the present invention. In the present embodiment shown, an illustration of an incision 310 on a surgical site 320 for application of a wound closure system 100.

Figure 4:
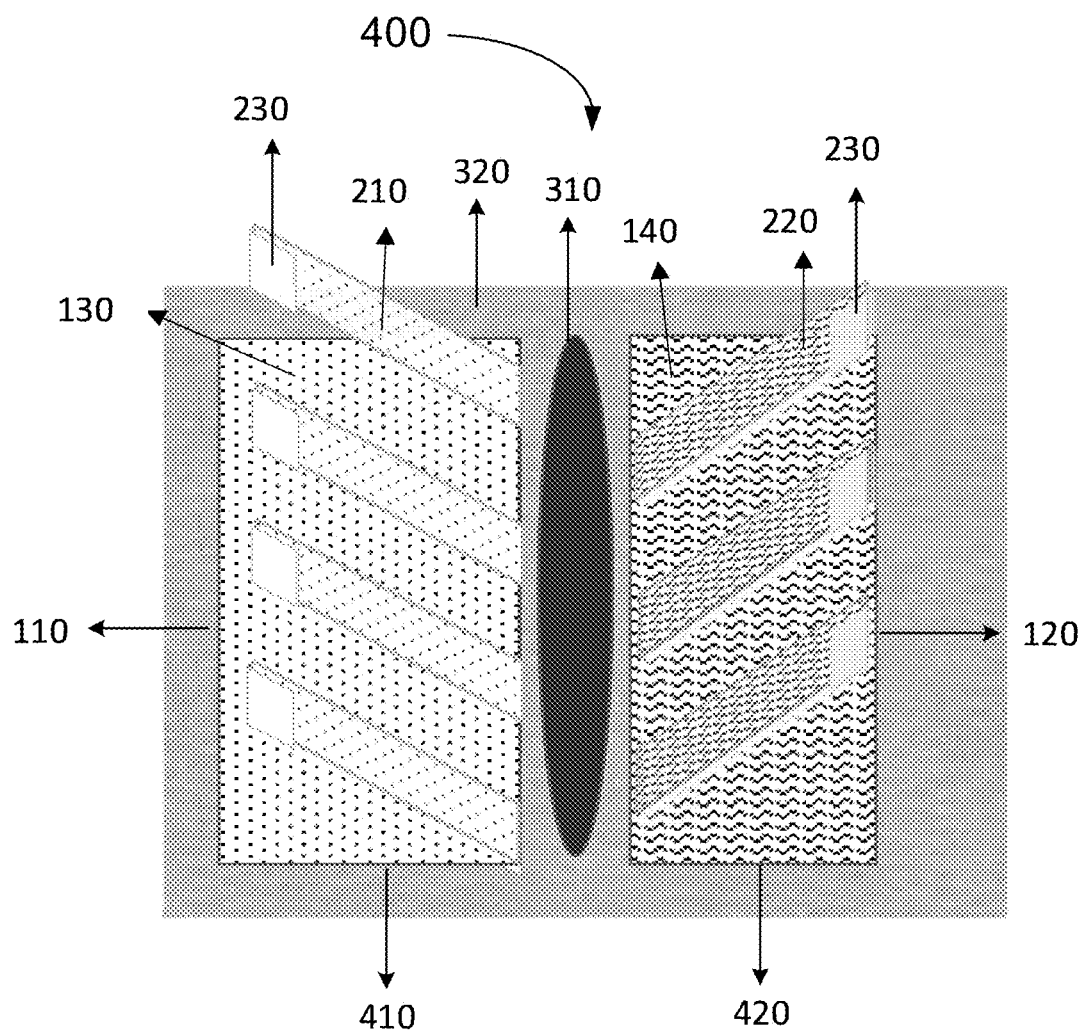
FIG. 4 is an illustration of the Reversible Wound Closure System applied to the surgical incision site, in accordance with an embodiment of the present invention.

FIG. 4 is an illustration 400 of a Reversible Wound Closure System 100 applied to a surgical incision site 310, in accordance with an embodiment of the present invention. In the present embodiment shown, the Reversible Wound Closure System 100 may be applied to the incision 310 at the surgical incision site 320. The skin compatible self-adhesive material disposed on the under surface portions of the first and second base sheet 110 120 may adhere to a surface of the surgical incision site 310, on both sides of the incision 310. The skin compatible self-adhesive material disposed on the under surface portion of the first base sheet 110 may be applied on a first portion 410 of the surgical incision site 320, adjacent the incision 310. The skin compatible self-adhesive material disposed on the under surface portion of the second base sheet 120 may be applied on a second portion 420 of the surgical incision site 320, adjacent the incision 310, opposite the first base sheet 110, and sandwiching the incision 310. The interlacing/interweaving strip sections 150 160 may be drawn together by pulling the strip sections 150 160 in opposite directions to draw the edges of the incision 310 together and may be pressed down against the commensurate, mating materials on the base sheets, locking the system in its closed position, thus keeping the incision closed with horizontal closure from both sides of the incision 310.

Figure 5:
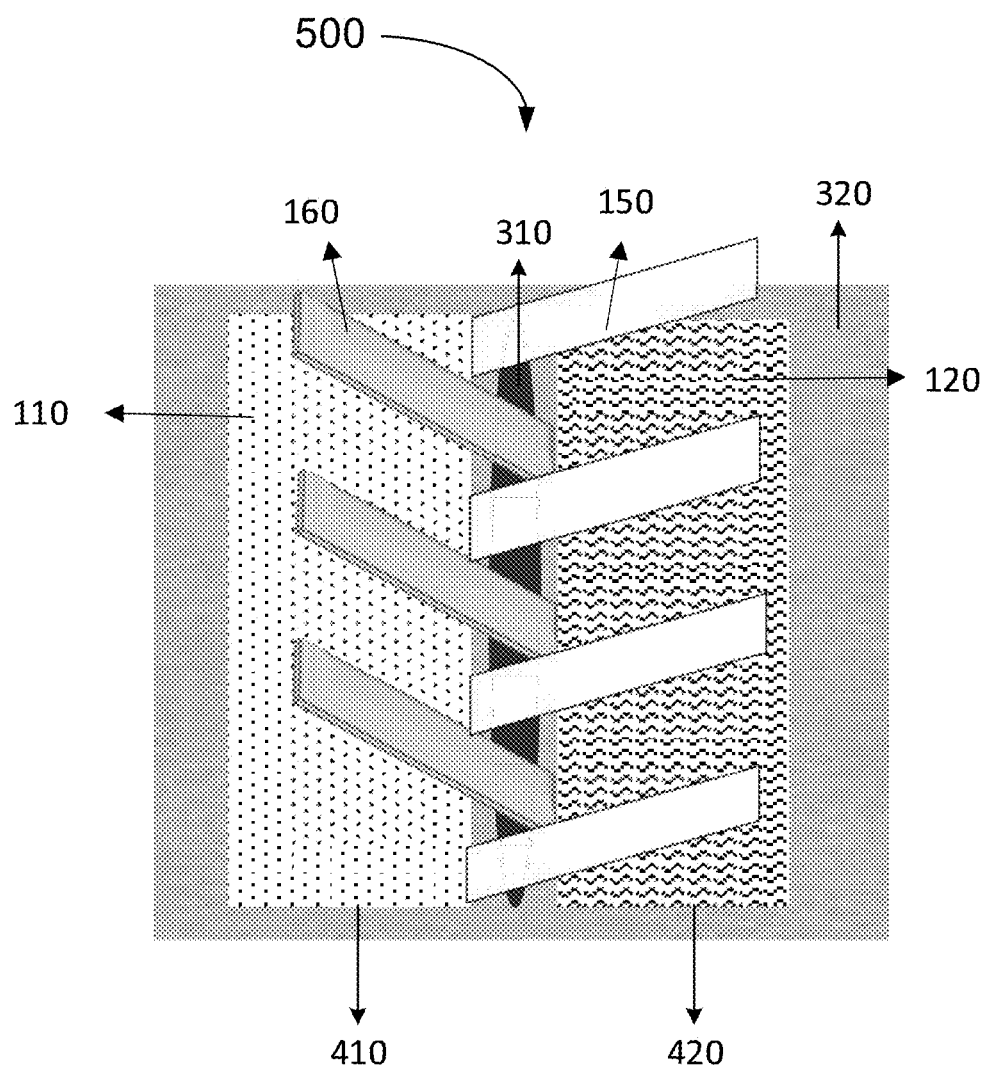
FIG. 5 is an illustration of interlacing strips of a Closure System in a wound closure operation, in accordance with an embodiment of the present invention.

FIG. 5 is an illustration 500 of interlacing the strips of a Reversible Wound Closure System 100 in an incision closure operation, in accordance with an embodiment of the present invention. In the present embodiment shown, the edges of incision 310 may be drawn together by pulling the strip sections 150 160 in opposite directions, but not limited to, interlacing or interweaving pattern. In one embodiment, the strip sections 150 160 may be drawn one (1) at a time in opposite directions but not limited to interlacing or interweaving pattern, which may draw the edges of the incision 310 together. In other embodiments, the strip sections 150 160 may be drawn two (2) or more at a time in opposite directions in interlacing or interweaving pattern, which may draw the edges of the incision 310 together. In some embodiments, the strip sections 150 160 may all be drawn together, at a time, in opposite directions but not limited to interlacing or interweaving pattern, which may draw the edges of the incision 310 together.

Figure 6:
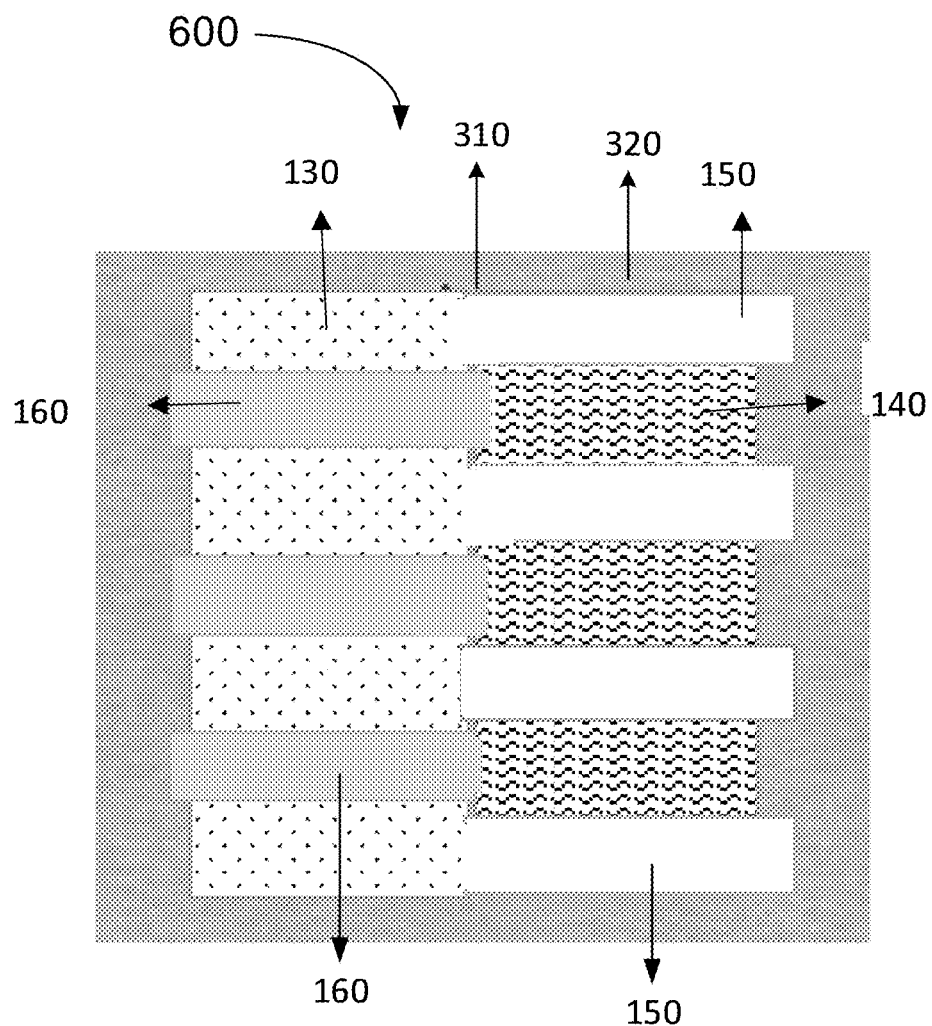
FIG. 6 is a top view of the Reversible Wound Closure System applied to a surgical incision site, in accordance with an embodiment of the present invention.

FIG. 6 is a top view 600 of the Reversible Wound Closure System 100 applied to a surgical incision site, in accordance with an embodiment of the present invention. In the present embodiment shown, the array of hook materials 210 of the first plurality of strip sections 150 may be into engagement with the array of mating loop materials 140 disposed on the upper surface of the second base sheet 120 but not limited to interlacing or interweaving pattern. And, the array of loop materials 220 of the second plurality of strip sections 160 may be into engagement with the array of hook materials 130 disposed on the upper surface of the first base sheet 110 but not limited to interlacing or interweaving pattern, which may engage the edges of the incision 310 together. The strip sections 150 160 may be pressed down against the commensurate, mating materials on the base sheets 110 120, locking the system in its closed position, thus keeping the incision closed with horizontal closure from both sides of the incision 310.

Figure 7:
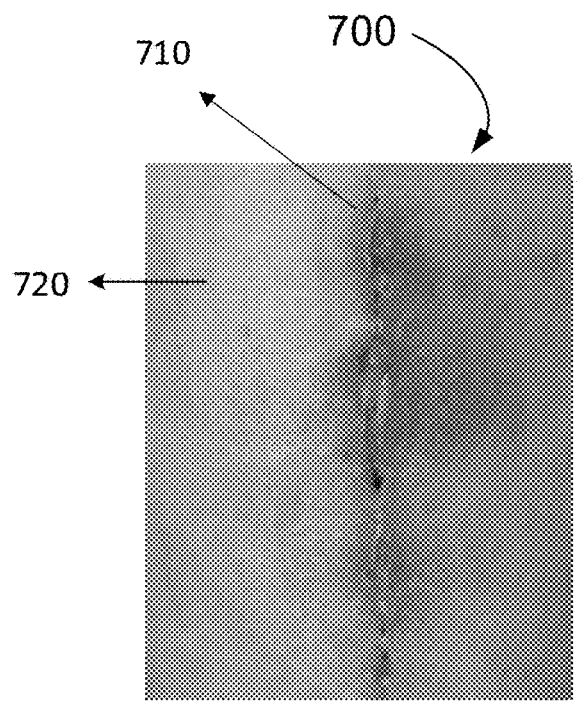
FIG. 7 is an illustration of an exemplary infected wound, in accordance with an embodiment of the present invention.

FIG. 7 is an illustration of an exemplary wound or laceration 700, in accordance with an embodiment of the present invention. In the present embodiment shown, an illustration of a wound 710 on a site 720 for application of a wound closure system 100. The wound 710 may have wide open edges, infected and in need of urgent care.

Figure 8:
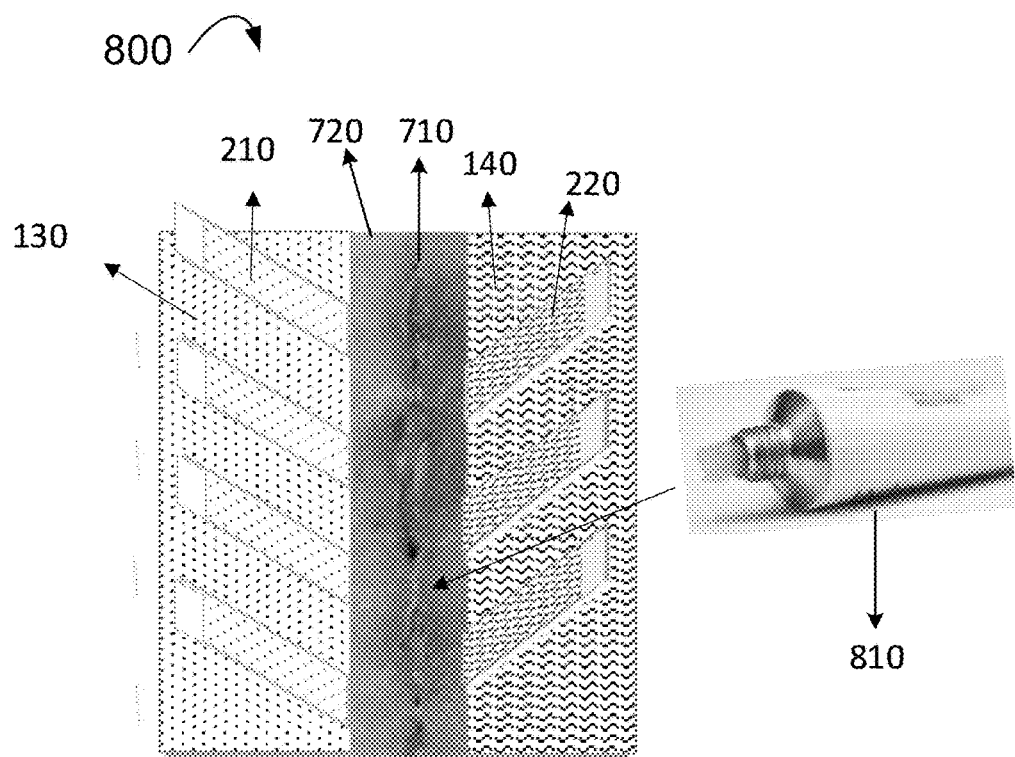
FIG. 8 is an illustration of application of topical antibiotics to the infected wound before wound closure, in accordance with an embodiment of the present invention.

FIG. 8 is an illustration 800 of application of topical antibiotics to the infected wound before and after a wound closure procedure, in accordance with an embodiment of the present invention. In the present embodiment shown, the system may allow application/renewal of topical agents or wound care products such as topical antibiotics to promote healing while maintaining wound closure and without removing/replacing the closure system. Topical agents or wound care products may be applied stepwise as the strip sections 150 160 are opened and closed consecutively during a wound healing process. The topical antibiotics 810 may be applied to a wound 710 on a site 720 before an application of a wound closure system 100 (e.g. as discussed above). In some embodiment, the topical antibiotics 810 may be applied to a healing wound 710 after the system is locked in its closed position by opening the strip sections 150 160, leaving the base sheets 110 120 intact, and applying the topical antibiotics 810. After application of the topical antibiotics 810, the strip sections 150 160 may be closed. The edges of the wound 710 may be drawn closer together by pulling the strips 150 160 in opposite directions then pressing the strip sections 150 160 down against the commensurate and mating materials on the base sheets 110 120 to lock the system in its closed position (e.g. as shown in FIG. 6).

Figure 9:
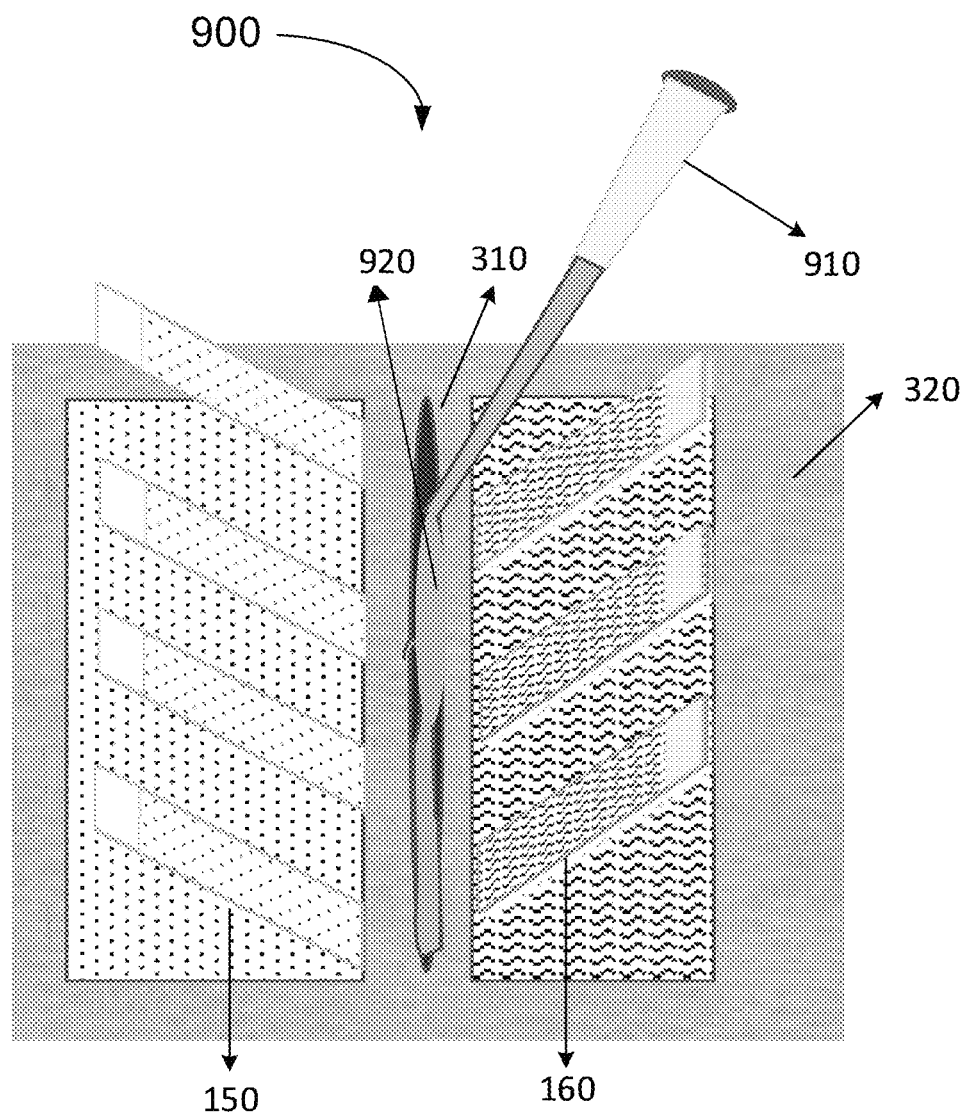
FIG. 9 is an illustration of an application of a skin adhesive to a laceration site before wound closure, in accordance with an embodiment of the present invention.

FIG. 9 is an illustration 900 of an application of a skin adhesive to a laceration site before and after a laceration site closure, in accordance with an embodiment of the present invention. In the present embodiment shown, the system may allow the application/renewal of topical agents or wound care products such as skin adhesive to promote healing while maintaining laceration site closure and without removing/replacing the closure system. The topical agents or wound care products may be applied stepwise as the strip sections 150 160 are opened and closed consecutively during a laceration site healing process. The skin adhesive 920 in a container 910 may be applied to the laceration 310 on a surgical site 320 before application of a wound closure system 100 (as discussed above). In some embodiment, the skin adhesive 920 may be applied to a healing laceration site 310 after the system is locked in its closed position by opening the strip sections 150 160, leaving the base sheets 110 120 intact, and applying the skin adhesive 920. After application of the skin adhesive 920, the strip sections 150 160 may be closed. The edges of the laceration 310 may be drawn closer together by pulling the strips 150 160 in opposite directions then pressing the strip sections 150 160 down against the commensurate and mating materials on the base sheets 110 120 to lock the system in its closed position (e.g. as shown in FIG. 6).

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" or "steps for" claim limitation implies that the broadest initial search on 35 USC § 112(6) (post AIA 112(f)) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112(6) (post AIA 112(f)) when such corresponding structures are not explicitly disclosed in the foregoing patent specification. Therefore, for any invention element(s)/structure(s) corresponding to functional claim limitation(s), in the below claims interpreted under 35 USC § 112(6) (post AIA 112(f)), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112(6) (post AIA 112(f)) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112(6) (post AIA 112(f)), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing a method and reversible, non-invasive, closing device for various types of surgical incisions, non-surgical incisions, traumatic lacerations, and various types and shapes of wounds that may require closure of the wound and stop a spread of infection, according to the present invention will be apparent to those skilled in the art. Various aspects of the invention have been described above by way of illustration, and the specific embodiments disclosed are not intended to limit the invention to the particular forms disclosed. The particular implementation of the method and reversible, non-invasive, closing device for various types of surgical incisions, non-surgical incisions, traumatic lacerations, and various types and shapes of wounds that may require closure of the wound and stop a spread of infection may vary depending upon the particular context or application. By way of example, and not limitation, the method and reversible, non-invasive, closing device for various types of surgical incisions, non-surgical incisions, traumatic lacerations, and various types and shapes of wounds that may require closure of the wound and stop a spread of infection described in the foregoing were principally directed to wound/incission/laceration closure implementations; however, similar techniques may instead be applied to cracked furnitures, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

What is claimed is:

1. A system comprising:
   a skin adhesive;
   a container that is configured to hold said skin adhesive, wherein said container is configured to be operable for applying said skin adhesive to a wound or incision;
   a first base sheet including an upper surface portion and an under surface portion, in which said first base sheet is configured to be disposed on a proximate vicinity of said wound or incision;
   an array of a first engaging material disposed on said upper surface portion of said first base sheet;
   a skin compatible self-adhesive material disposed on the under surface portion of said first base sheet, said skin compatible self-adhesive material is configured to affix said first base sheet to skin;
   a second base sheet having a proximate upper surface and under surface portions, in which said second base sheet is configured to be disposed on a proximate vicinity of the wound or incision, adjacent the vicinity of said first base sheet;
   an array of a second engaging material disposed on said upper surface portion of the second base sheet;
   a skin compatible self-adhesive material disposed on the under surface portion of said second base sheet said skin compatible self-adhesive material is configured to affix said second base sheet to skin;
   a first plurality of individual strip sections extending out of said first base sheet, wherein said first plurality of individual strip sections are operable for engagement and disengagement with said second base sheet;
   a second plurality of individual strip sections extending out of the second base sheet, wherein said second plurality of individual strip sections are operable for engagement or disengagement with said first base sheet;
   said second plurality of individual strip sections are configured to interweave with said first plurality of individual strip sections, wherein said first and second plurality of individual strip sections are configured to be pulled in opposing directions to draw an edge portion of the wound or incision together; and
   wherein said first and second plurality of individual strip sections engages with said first and second base sheets to generally close the edge portion of the wound or incision together, to substantially aid in a closure and healing of the wound or incision.

* * * * *